United States Patent [19]

Britton et al.

[11] 4,093,805
[45] June 6, 1978

[54] 4-HYDROXY-3,4-DIHYDRO-2(1H)-QUINAZOLINETHIONES

[75] Inventors: Thomas C. Britton; Donald L. Trepanier, both of Midland, Mich.

[73] Assignee: The Dow Chemical Company, Midland, Mich.

[21] Appl. No.: 769,480

[22] Filed: Feb. 17, 1977

[51] Int. Cl.² .......................................... C07D 413/06
[52] U.S. Cl. .................................. 544/116; 544/285; 424/248.51; 424/251
[58] Field of Search ................. 544/116; 260/256.5 R

[56] References Cited
PUBLICATIONS

Kawai "Chem. Abstracts" vol. 73 (1970) No. 87935n.

Primary Examiner—Henry R. Jiles
Assistant Examiner—R. W. Ramsuer
Attorney, Agent, or Firm—James W. Ambrosius

[57] ABSTRACT

A two-step process for preparing quinazolinethiones by reacting a 2-aminobenzophenone with thiophosgene to give a 2-benzoylisothiocyanate and treating this compound with a predetermined primary amine. A series of substituted quinazolinethiones which display antidepressant and antianxiety properties also are disclosed.

10 Claims, No Drawings

4-HYDROXY-3,4-DIHYDRO-2(1H)-QUINAZOLINETHIONES

BACKGROUND OF THE INVENTION

Quinazolinethiones and quinazolinones prepared by treating 2-amino-5-chlorobenzophenone with either an isothiocyanate or an isocyanate have been described as sedatives, diuretics and blood pressure depressants. Japanese publication 70 16,950 (CA73:87935n). See also Nippon Kagaku Zasshi 90(9), 917–20 (1969). Other quinazalinethiones derived from 2-thio-4-hydroxy-1,2,3,4-tetrahydroquinazoline have been disclosed by Gheorghiu and Arventi in *Bull Soc. Chim.* [5], 5, 38–43 (1938), see also *J. Hetero Chem.* 3, 535–36 (1966). Anti-inflammatory properties have also been attributed to certain quinazaline-2(1H)-thiones. See Derwent Abstract U.S. B368862.

Quinazalinones have also been described in *Yakugaku Zasshi*, 90(5), 629–33 (1970); British Pat. No. 1,343,668; and Japanese Publication No. 70 41,590 (CA75:5934r).

SUMMARY OF THE INVENTION

The present invention relates to a method for preparing compounds having the general formula:

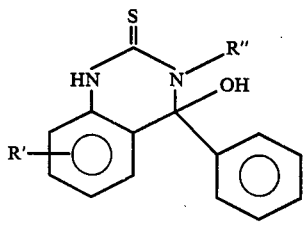

I wherein R' represents alkyl, halo, hydrogen, and alkoxy. R" represents alkyl, alkene, alkyne, hydroxyalkyl, phenyl, substituted phenyl, amino, dialkylaminoalkyl, cycloalkylaminoalkyl and 4-morpholinylalkyl. As used herein, unless otherwise specified, the term alkyl refers to an alkyl group having from one to four carbon atoms. In addition, the terms alkene and alkyne refer to moieties having from 2 to 4 carbon atoms in a chain.

Compounds described above are prepared by a novel two-step process wherein a 2-aminobenzophenone is reacted with thiophosgene to give a 2-benzoylphenylisothiocyanate. The benzoylphenylisothiocyanate is treated with a predetermined primary amine to give the desired quinazolinethione. The general reaction sequence may be summarized as follows:

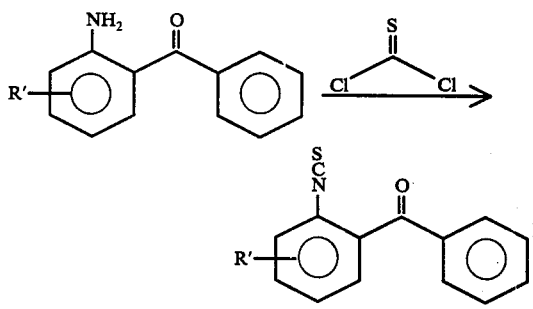

II

-continued

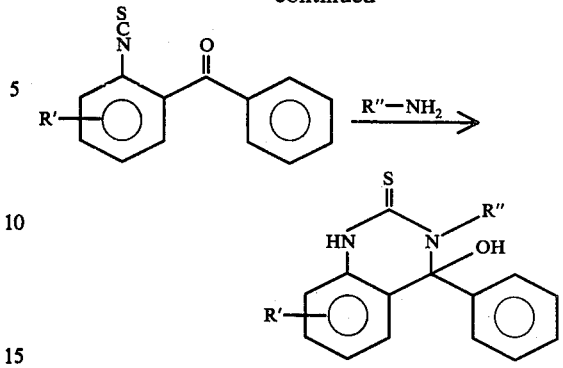

III wherein R' and R" represent the same groups as described above.

As will be demonstrated in the examples, the above process offers a simple, practical, and efficient method of preparing compounds of formula I above.

Using the general procedure described above, a number of novel compounds were prepared which exhibited Central Nervous System Activity, especially antidepressant and antianxiety activity in mammals. The compounds were prepared from 2-amino-5-chlorobenzophenone and R" of formula I above was selected from the group including amino, dialkylaminoalkyl, cycloalkylaminoalkyl and 4-morpholinylalkyl. These compounds differ from compounds known in the prior art in the presence of the amino moieties substituted at the 3-position.

The invention also includes the pharmaceutically-acceptable salts of the novel quinazolinethione compounds used in the practice of the present invention. As used in the specification and claims, the term "pharmaceutically-acceptable salts" refers to non-toxic acid addition salts of the quinazolinethione compounds, the anions of which are relatively innocuous to animals at dosages consistent with good antidepressant and antianxiety activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

DETAILED DESCRIPTION OF THE INVENTION

EXAMPLE 1

Preparation of the Intermediate 2-benzoyl-4-chlorophenylisothiocyanate

A five liter, 3-necked, round-bottom flask equipped with a condenser plus scrubber, mechanical stirrer, and dropping funnel was used as the reaction vessel. The reaction vessel was cooled in an ice bath after charging with 1.2 liters of water. After the water had cooled, 126 ml (1.65 moles) of thiophosgene was added. The mixture was stirred vigorously while a solution containing 352 grams (1.52 moles) of 2-amino-5-chlorobenzophenone in about 1 liter of methylene chloride was added over a period of 20 to 25 minutes. After addition was complete the funnel was rinsed with about 150 ml of methylene chloride and the reaction mixture was stirred for about one hour with the ice bath in place. Then the ice bath was removed and the reaction mixture was stirred for one additional hour. The organic phase was separated, dried with magnesium sulfate, and concentrated in vacuo. The 2-benzoyl-4-chlorophenylisothiocyanate remained behind as a brown oil which solidified on cooling. The product was recrystallized from hexane to yield tan crystals.

Other intermediates which exemplify those that could be used to prepare quinazolinethiones of formula I using the general method described above are the compounds:
2-benzoylphenylisothiocyanate
2-benzoyl-4-bromophenylisothiocyanate
2-benzoyl-4-methylphenylisothiocyanate

EXAMPLE 2

Preparation of 3-amino-6-chloro-3,4-dihydro-4-hydroxy-4-phenyl-2(1H)-quinazolinethione The ice cooled reaction vessel was charged with 1.0 ml of hydrazine in about 100 ml of isopropanol. A solution containing 5.48 grams (0.02 mole) of the 2-benzoyl-4-chlorophenylisothiocyanate prepared in Example 1 above dissolved in about 50 ml of ethyl ether was added dropwise to the vessel. The mixture was stirred at ice bath temperatures for about 20 minutes following addition of the hydrazine and for an additional one hour at ambient temperatures. The 3-amino-6-chloro-3,4-dihydro-4-hydroxy-4-phenyl-2(1H)-quinazolinethione precipitated as a white solid. The crude product (yield 88%) was washed with and recrystallized from isopropanol to yield a powdery white solid.

Elemental analysis yielded values of carbon 55.04%, hydrogen 3.83%, nitrogen 13.75%, and sulfur 10.4% as compared to calculated values of carbon 54.99%, hydrogen 3.96%, nitrogen 13.74%, and sulfur 10.4%. The melting point was found to be 182°–184° C.

EXAMPLE 3

Preparation of 6-chloro-3,4-dihydro-4-hydroxy-3-(2-hydroxyethyl)-4-phenyl-2(1H)-quinazolinethione Using the general procedure already described above, a solution containing 10.92 grams (40 moles) of 2-benzoyl-4-chlorophenylisothiocyanate in about 100 ml of ethyl ether was added dropwise to a stirred solution of 2.83 grams (44 moles) of ethanolamine in 200 ml of isopropanol. The reaction mixture was stirred overnight. The 6-chloro-3,4-dihydro-4-hydroxy-3-(2-hydroxyethyl)-4-phenyl-2(1H)-quinazolinethione precipitated as a white solid. The product was washed with a mixture of ethyl ether and isopropanol to give the final product which had a melting point of 238°–240° C. Final yield was 93%.

Elemental analysis yielded carbon 57.22%, hydrogen 4.47%, nitrogen 8.22%, and sulfur 9.70% as compared to theoretical values of carbon 57.39%, hydrogen 4.52%, nitrogen 8.37%, and sulfur 9.58%.

One skilled in the art will recognize that the process outlined above can be used as a general procedure for making compounds having the general structure shown in formula I described earlier.

Compounds actually prepared using the procedure outlined above are shown in Table I. All of the compounds were prepared from 2-amino-4-chlorobenzophenone, therefore R' is 6-chloro on all the compounds. Other substitutions already described would also be operable.

TABLE I

| Example | R'' | Mp (° C) | Yield (%) | Formula | Analysis* C | H | N | S |
|---|---|---|---|---|---|---|---|---|
| 4 | —CH$_2$CH=CH$_2$ | 188–190 dec | 80 | C$_{17}$H$_{15}$ClN$_2$OS | 61.7 (61.72) | 4.70 (4.57) | 8.68 (8.48) | |
| 5 | —CH$_2$C≡CH | 194–6 dec | 91 | C$_{17}$H$_{13}$ClN$_2$OS | 61.95 (62.10) | 3.95 (3.99) | 8.44 (8.52) | |
| 6 | —(CH$_2$)$_2$—N(CH$_3$)$_2$ | 143–5 dec | 71 | C$_{18}$H$_{20}$ClN$_3$OS | 59.77 (59.74) | 5.55 (5.57) | 11.60 (11.61) | 8.87 (8.86) |
| 7 | —(CH$_2$)$_3$—N(CH$_3$)$_2$ | 149–154 dec | 95 | C$_{19}$H$_{22}$ClN$_3$OS | 60.62 (60.70) | 6.05 (5.90) | 10.90 (11.18) | 8.43 (8.53) |
| 8 | —(CH$_2$)$_2$—N(C$_2$H$_5$)$_2$ | 135–7 dec | 57 | C$_{20}$H$_{24}$ClN$_3$OS | 61.69 (61.60) | 6.29 (6.20) | 10.80 (10.78) | 8.19 (8.22) |
| 9 | —(CH$_2$)$_3$—N(C$_2$H$_5$)$_2$ | 177–8 dec | 93 | C$_{21}$H$_{26}$ClN$_3$OS | 62.38 (62.44) | 6.60 (6.49) | 10.51 (10.40) | 8.02 (7.94) |
| 10 | —(CH$_2$)$_2$—N⟨pyrrolidinyl⟩ | 192–4 dec | 84 | C$_{21}$H$_{24}$ClN$_3$OS | 62.82 (62.75) | 5.99 (6.02) | 10.50 (10.45) | 7.91 (7.98) |
| 11 | —(CH$_2$)$_2$—N⟨morpholinyl⟩ | 197–8 dec | 94 | C$_{20}$H$_{22}$ClN$_3$O$_2$S | 59.37 (59.47) | 5.54 (5.49) | 10.28 (10.40) | 7.81 (7.94) |
| 12 | —(CH$_2$)$_3$—N⟨morpholinyl⟩ | 200–2 dec | 97 | C$_{21}$H$_{24}$ClN$_3$O$_2$S | 60.60 (60.35) | 5.84 (5.79) | 10.15 (10.05) | 7.55 (7.67) |

*Theoretical Values are given in parenthesis.

Although compounds such as 6-chloro-3,4-dihydro-4-hydroxy-4-phenyl-3-(2-propenyl)-2(1H)-quinazolinethione (Example 4) have been described in the literature and their utility established, novel compounds falling within formula I above were also prepared. These compounds wherein R'' is amino, dialkylaminoalkyl, cycloalkylaminoalkyl, and 4-morpholinylalkyl were found to have antidepressant and antianxiety properties when administered internally to mammals. Specific compounds exhibiting these properties are:

3-amino-6-chloro-3,4-dihydro-4-hydroxy-4-phenyl-2(1H)-quinazolinethione (Example 1).

6-chloro-3-(2-(dimethylamino)ethyl)-3,4-dihydro-4-hydroxy-4-phenyl-2(1H)-quinazolinethione (Example 6).

6-chloro-3-(3-dimethylamino)propyl-3,4-dihydro-4-hydroxy-4-phenyl-2(1H)-quinazolinethione (Example 7).

6-chloro-3-(2-diethylamino)-3,4-dihydro-4-hydroxy-4-phenyl-2(1H)-quinazolinethione (Example 8).

6-chloro-3-(2-(dimethylamino)ethyl)-3,4-dihydro-4-hydroxy-4-phenyl-2(1H)-quinazolinethione (Example 9).

6-chloro-3,4-dihydro-4-hydroxy-4-phenyl-3(2-(1-piperidinyl)ethyl)-2(1H)-quinazolinethione (Example 10).

6-chloro-3,4-dihydro-4-hydroxy-3-(2-(4-morpholinyl)ethyl)-4-phenyl-2(1H)-quinazolinethione (Example 11).

6-chloro-3,4-dihydro-4-hydroxy-3-(3-(4-morpholinyl)propyl)-4-phenyl-2(1H)-quinazolinethione (Example 12).

As noted above, the novel 4-hydroxy-3,4-dihydro-2(1H)-quinazolinethiones are active on the central nervous system when administered internally to a mammal in a psychoactively-effective amount. Member compounds have been found to be particularly useful as antidepressant/antianxiety agents when used in accordance with the present invention.

In practicing the method of the invention, one or more compounds of the present invention are administered internally to a mammal by a route effective to introduce an effective psychoactive amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood via the gastrointestinal tract. The compounds are orally effective, and generally have a high ratio of toxic dose to effective dose when orally administered and this route is preferred. The term psychoactive amount refers to the amount of the compound which is administered to the mammal to induce the desired central nervous system response. For example, an effective antidepressant or antianxiety amount is the amount sufficient to alleviate central nervous system depression or anxiety, respectively.

The psychoactive amount of the compound, that is, the amount of the compound sufficient to provide the desired effect, depends on various known factors such as the size, type, age and condition of the animal to be treated, the particular compound or compounds of the invention employed, the route and frequency of administration, the type and degree of central nervous system condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at a dosage rate of from about 10 to about 150 mg/kg of bodyweight with about 20 to about 60 being preferred. Higher dosage rates may be employed, for example, when the compound is administered orally in a timed release dosage form. When administered by injection, good results are obtained with an amount of from about 10 to about 6 milligrams of the compound per kilogram of animal bodyweight. From about 20 to 150 milligrams of the active compound per kilogram, depending on dosage unit form employed, provide good results when the compound is administered orally. In the case of mammals suffering from central nervous system depression/anxiety (exhibiting symptoms of depression/anxiety), administration of an antidepressant/antianxiety amount of the compound is preferably repeated at predetermined intervals. It is generally desirable to administer the individual dosages at the lowest antidepressant/anxiety amount which provides the desired continuity consonant with a convenient dosing schedule. In a convenient repetitive procedure, the compounds are administered in single or divided oral doses at daily rates of about 20 to 150 milligrams per kilogram per day.

In practicing the method of the invention, the active ingredient is preferably incorporated in a composition comprising a pharmaceutical carrier and from about 0.001 to about 95 percent by weight of the compound. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active compound can be formulated in conventional timed release capsule or tablet formulations.

Preferred compositions include sterile injectable solutions containing from about 0.001 to about 10 percent by weight of the compound in a pharmaceutical carrier suitable for injection, such as isotonic saline solution, Ringer's Injection USP, and lactated Ringer's USP, and the like.

EXAMPLE 13

A group of four mice were administered 60 mg/kg of the compound 6-chloro-3-(2-(dimethylamino)-ethyl)-3,4-dihydro-4-hydroxy-4-phenyl-2(1H)-quinazolinethione (Example 7) by intraperitoneal injection via an aqueous carrier. A similar group of mice serving as controls were injected only with the carrier. After 30 minutes, both groups of mice were injected subcutaneously with 2.5 mg/kg of reserpine. The administration of reserpine to the control mice resulted in a classical progression of symptoms beginning with a dropping of the eyelids (ptosis) and later culminating in a generalized depression with decreased spontaneous motor activity and decreased responsiveness to auditary and tacticle stimuli.

Animals injected with the benzotriazepine compound were graded after 45 minutes on the following basis: no ptosis = 0, partial ptosis = 1, complete ptosis = 2. Adding the grades for the four test mice gave a value of 4 out of a possible 8 or 50% protection against reserpine-induced ptosis. The value for the four control mice was 8.

EXAMPLE 14

Antidepressant activity may also be illustrated in vitro by measuring the uptake of the neurotransmittors norepinephrine and serotonin in synaptosome preparations prepared from the forebrains of rats. The synaptosome preparation is incubated at 37° C with radioactive neurotransmittor and the test compound at a concentration of 10 μg/ml. The synaptosome are isolated and the uptake of labelled neurotransmittor measured by liquid scintillation spectrometry using standard techniques. Percent inhibition of uptake is determined by comparing the radioactivity taken in the synaptosome preparation with that of a similarly incubated saline control. Low values indicate activity. Using this technique, the compound 6-chloro-3-(2-diethylamino)ethyl)-3,4-dihydro-4-hydroxy-4-phenyl-2(1H)-quinazolinethione (Example 8) showed 3% inhibition of norepinephrine and 7% inhibition of seratonin uptake.

EXAMPLE 15

Compounds exhibiting antianxiety properties block the stress induced rise of serum corticosteroid levels. See *British Medical Journal,* 1971(2), p. 310–313. Corticosteroid levels were compared between stressed male rats pretreated with 10 mg/kg given by intraperitoneal injection to corticosteroid levels of stressed male rats pretreated with saline. The results were expressed as a ratio with values less than 1.0 indicative of activity. The compound 6-chloro-3,4-dihydro-4-hydroxy-3-(3-(4-morpholinyl)propyl)-4-phenyl-2(1H)-quinazolinethione (Example 12) gave a value of 0.12. Other compounds described within the scope of the present invention, although less active, also showed significant antianxiety properties when used in the above test.

We claim:

1. A compound of the formula

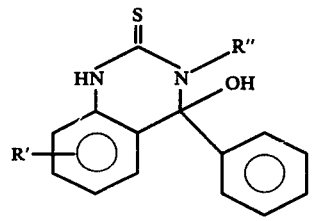

wherein R' represents alkyl, halo, and hydrogen, and R" represents amino, dialkylaminoalkyl, (pyrrolidinyl)ethyl, (piperidinyl)ethyl and 4-morpholinylalkyl and further including the pharmaceutically-acceptable salts thereof and wherein any alkyl refers to a moiety having from 1 to 4 carbon atoms.

2. The compound of claim 1 wherein R' is in the 6 position.

3. The compound of claim 2 which is 3-amino-6-chloro-3,4-dihydro-4-hydroxy-4-phenyl-2(1H)-quinazolinethione and the pharmaceutically-acceptable salts thereof.

4. The compound of claim 2 which is 6-chloro-3-(2-(dimethylamino)ethyl)-3,4-dihydro-4-hydroxy-4-phenyl-2(1H)-quinazolinethione and the pharmaceutically-acceptable salts thereof.

5. The compound of claim 2 which is 6-chloro-(3-(3-dimethylamino)propyl)-3,4-dihydro-4-hydroxy-4-phenyl-2(1H)-quinazolinethione and the pharmaceutically-acceptable salts thereof.

6. The compound of claim 2 which is 6-chloro-3-(2-(diethylamino)propyl)-3,4-dihydro-4-hydroxy-4-phenyl-2(1H)-quinazolinethione and the pharmaceutically-acceptable salts thereof.

7. The compound of claim 2 which is 6-chloro-3-(2-(dimethylamino)ethyl)-3,4-dihydro-4-hydroxy-4-phenyl-2(1H)-quinazolinethione and the pharmaceutically-acceptable salts thereof.

8. The compound of claim 2 which is 6-chloro-3,4-dihydro-4-hydroxy-4-phenyl-3-(2-(1-piperidinyl)ethyl)-2(1H)-quinazolinethione and the pharmaceutically-acceptable salts thereof.

9. The compound of claim 2 which is 6-chloro-3,4-dihydro-4-hydroxy-3-(2-(4-morpholinyl)ethyl)-4-phenyl-2(1H)-quinazolinethione and the pharmaceutically-acceptable salts thereof.

10. The compound of claim 2 which is 6-chloro-3,4-dihydro-4-hydroxy-3-(3-(4-morpholinyl)propyl)-4-phenyl-2(1H)-quinazolinethione and the pharmaceutically-acceptable salts thereof.

* * * * *

UNITED STATES PATENT AND TRADEMARK OFFICE
CERTIFICATE OF CORRECTION

PATENT NO. : 4,093,805
DATED : June 6, 1978
INVENTOR(S) : Thomas C. Britton, et al.

It is certified that error appears in the above-identified patent and that said Letters Patent are hereby corrected as shown below:

Column 1, line 20 "B368862" should read -- B368-862 --;

Column 5, line 41 "high" should read -- higher --.

Signed and Sealed this

Twenty-sixth Day of December 1978

[SEAL]

Attest:

RUTH C. MASON
Attesting Officer

DONALD W. BANNER
Commissioner of Patents and Trademarks